United States Patent
Moghari et al.

(10) Patent No.: US 9,271,661 B2
(45) Date of Patent: Mar. 1, 2016

(54) METHOD FOR FREE-BREATHING MAGNETIC RESONANCE IMAGING USING ITERATIVE IMAGE-BASED RESPIRATORY MOTION CORRECTION

(75) Inventors: Mehdi Hedjazi Moghari, Cambridge, MA (US); Reza Nezafat, Newton, MA (US)

(73) Assignee: BETH ISRAEL DEACONESS MEDICAL CENTER, INC, Boston, MA (US)

( * ) Notice: Subject to any disclaimer, the term of this patent is extended or adjusted under 35 U.S.C. 154(b) by 538 days.

(21) Appl. No.: 13/360,979

(22) Filed: Jan. 30, 2012

(65) Prior Publication Data
US 2013/0197347 A1     Aug. 1, 2013

(51) Int. Cl.
| | |
|---|---|
| *A61B 5/055* | (2006.01) |
| *A61B 5/00* | (2006.01) |
| *G01R 33/565* | (2006.01) |
| *G01R 33/567* | (2006.01) |

(52) U.S. Cl.
CPC ............ *A61B 5/055* (2013.01); *A61B 5/7207* (2013.01); *G01R 33/56509* (2013.01); *G01R 33/5676* (2013.01)

(58) Field of Classification Search
CPC .................................................. G01R 33/5676
USPC ......................................................... 600/410
See application file for complete search history.

(56) References Cited

U.S. PATENT DOCUMENTS

| | | | | |
|---|---|---|---|---|
| 7,941,204 | B1 * | 5/2011 | Wang et al. .................... | 600/420 |
| 2003/0050554 | A1 * | 3/2003 | Schaffer ........................ | 600/410 |
| 2012/0245453 | A1 * | 9/2012 | Tryggestad et al. .......... | 600/413 |

OTHER PUBLICATIONS

Batchelor, et al., Matrix Description of General Motion Correction Applied to Multishot Images, Magnetic Resonance in Medicine, 2005, 54(5):1273-1280.
Bhat, et al., 3D Radial Sampling and 3D Affine Transform-Based Respiratory Motion Correction Technique for Free-Breathing Whole-Heart Coronary Mra with 100% Imaging Efficiency, Magnetic Resonance in Medicine, 2011, 65 (5):1269-1277.
Danias, et al., Prospective Navigator Correction of Image Position for Coronary MR Angiography, Radiology, 1997, 203:733-736.
Ehman, et al., Influence of Physiologic Motion on the Appearance of Tissue in MR Images, Radiology, 1986, 159:777-782.
Felblinger, et al., Synchronization Device for Electrocardiography-Gated Echo-Planar Imaging, Radiology, 1995, 197:311-313.
Felblinger, et al., Electrocardiogram Acquisition During MR Examinations for Patient Monitoring and Sequence Triggering, Magnetic Resonance in Medicine, 1994, 32(4):523-529.

(Continued)

*Primary Examiner* — Jonathan Cwern
(74) *Attorney, Agent, or Firm* — Quarles & Brady, LLP

(57) ABSTRACT

A method for free-breathing magnetic resonance imaging (MRI) using iterative image-based respiratory motion correction is provided. An MRI system is used to acquired k-space data and navigator data from a subject. The k-space data is then sorted into a plurality of data bins using the navigator data. A motion correction parameter is estimated for each data bin and is applied to the respective k-space data in that bin. The corrected k-space data segments are then combined to form a corrected k-space data set, from which an image is reconstructed. The process may be iteratively repeated until an image quality metric is optimized; for example, until an image sharpness measure is sufficiently maximized.

15 Claims, 3 Drawing Sheets

(56) References Cited

OTHER PUBLICATIONS

Hauser, et al., Coronary MRI More Pretty Pictures or Present-Day Value?, Journal of American College of Cardiology, 2006, 48(10):1951-1952.

Henningsson, et al., Real-Time Adaptive Motion Correction for Coronary MR Angiography, Proc. Intl. Soc. Mag. Reson. Med., 2009, 17:4645.

Jhooti, et al., 3D Coronary Artery Imaging with Phase Reordering for Improved Scan Efficiency, Magnetic Resonance in Medicine, 1999, 41(3):555-562.

Jhooti, et al., Hybrid Ordered Phase Encoding (HOPE): An Improved Approach for Respiratory Artifact Reduction, Journal of Magnetic Resonance Imaging, 1998, 8(4):968-980.

Jhooti, et al., A Fully Automatic and Highly Efficient Navigator Gating Technique for High-Resolution Free-Breathing Acquisitions: Continuously Adaptive Windowing Strategy, Magnetic Resonance in Medicine, 2010, 64(4):1015-1026.

Kato, et al., Assessment of Coronary Artery Disease Using Magnetic Resonance Coronary Angiography, Journal of the American College of Cardiology, 2010, 56(12):983-991.

Keegan, et al., Non-Model-Based Correction of Respiratory Motion Using Beat-to-Beat 3D Spiral Fat-Selective Imaging, Journal of Magnetic Resonance Imaging, 2007, 26(3):624-629.

Kim, et al., Impact of Bulk Cardiac Motion on Right Coronary MR Angiography and Vessel Wall Imaging, Journal of Magnetic Resonance Imaging, 2001, 14(4):383-390.

Lai, et al., Respiratory Self-Gated Four-Dimensional Coronary MR Angiography: A Feasibility Study, Magnetic Resonance in Medicine, 2008, 59(6):1378-1385.

Lai, et al., A Respiratory Self-Gating Technique with 3D-Translation Compensation for Free-Breathing Whole-Heart Coronary MRA, Magnetic Resonance in Medicine, 2009, 62(3):731-738.

Larson, et al., Self-Gated Cardiac Cine MRI, Magnetic Resonance in Medicine, 2004, 51(1):93-102.

Manke, et al., Novel Prospective Respiratory Motion Correction Approach for Free-Breathing Coronary MR Angiography Using a Patient-Adapted Affine Motion Model, Magnetic Resonance in Medicine, 2003, 50(1):122-131.

McLEISH, et al., A Study of the Motion and Deformation of the Heart Due to Respiration, IEEE Transactions on Medical Imaging, 2002, 21(9):1142-1150.

Nehrke, et al., Prospective Correction of Affine Motion for Arbitrary MR Sequences on a Clinical Scanner, Magnetic Resonance in Medicine, 2005, 54(5):1130-1138.

Odille, et al., Generalized MRI Reconstruction Including Elastic Physiological Motion and Coil Sensitivity Encoding, Magnetic Resonance in Medicine, 2008, 59(6):1401-1411.

Odille, et al., Generalized Reconstruction by Inversion of Coupled Systems (GRICS) Applied to Free-Breathing MRI, Magnetic Resonance in Medicine, 2008, 60(1):146-157.

Sachs, et al., The Real-Time Interactive 3-D-DVA for Robust Coronary MRA, IEEE Transactions on Medical Imaging, 2000, 19(2):73-79.

Sachs, et al., The Diminishing Variance Algorithm for Real-Time Reduction of Motion Artifacts in MRI, Magnetic Resonance in Medicine, 1995, 34(3):412-422.

Sakuma, et al., Detection of Coronary Artery Stenosis With Whole-Heart Coronary Magnetic Resonance Angiography, Journal of the American College of Cardiology, 2006, 48(10):1946-1950.

Schmidt, et al., Highly Efficient Respiratory Gating in Whole Heart MR Employing Non-Rigid Retrospective Motion Correction, Proc. Intl. Soc. Mag. Reson. Med., 2010, 18:492.

Shechter, et al., Respiratory Motion of the Heart From Free Breathing Coronary Angiograms, IEEE Transactions on Medical Imaging, 2004, 23(8):1046-1056.

Shechter, et al., Displacement and Velocity of the Coronary Arteries: Cardiac and Respiratory Motion, IEEE Transactions on Medical Imaging, 2006, 25(3):369-375.

Sinkus, et al., Motion Pattern Adapted Real-Time Respiratory Gating, Magnetic Resonance in Medicine, 1999, 41(1):148-155.

Wang, et al., Respiratory Motion of the Heart: Kinematics and the Implications for the Spatial Resolution in Coronary Imaging, Magnetic Resonance in Medicine, 1995, 33:713-719.

Weiger, et al., Motion-Adapted Gating Based on k-space Weighting for Reduction of Respiratory Motion Artifacts, Magnetic Resonance in Medicine, 1997, 38(2):322-333.

\* cited by examiner

METHOD FOR FREE-BREATHING MAGNETIC RESONANCE IMAGING USING ITERATIVE IMAGE-BASED RESPIRATORY MOTION CORRECTION

STATEMENT REGARDING FEDERALLY SPONSORED RESEARCH

This invention was made with government support under EB008743 awarded by the National Institutes of Health. The government has certain rights in the invention.

BACKGROUND OF THE INVENTION

The field of the invention is magnetic resonance imaging (MRI) systems and methods. More particularly, the invention relates to methods for free-breathing cardiac MR imaging using iterative image-based respiratory motion correction.

MRI uses the nuclear magnetic resonance ("NMR") phenomenon to produce images. When a substance such as human tissue is subjected to a uniform magnetic field, such as the so-called main magnetic field, $B_0$, of an MRI system, the individual magnetic moments of the nuclei in the tissue attempt to align with this $B_0$ field, but precess about it in random order at their characteristic Larmor frequency, $\Omega$. If the substance, or tissue, is subjected to a so-called excitation electromagnetic field, $B_1$, that is in the plane transverse to the $B_0$ field and that has a frequency near the Larmor frequency, the net aligned magnetic moment, referred to as longitudinal magnetization, may be rotated, or "tipped," into the transverse plane to produce a net transverse magnetic moment, referred to as transverse magnetization. A signal is emitted by the excited nuclei or "spins," after the excitation field, $B_1$, is terminated, and this signal may be received and processed to form an image.

When utilizing these "MR" signals to produce images, magnetic field gradients ($G_x$, $G_y$, and $G_z$) are employed for spatial encoding. Typically, the region to be imaged is scanned by a sequence of measurement cycles in which these gradients vary according to the particular localization method being used. The resulting set of received MR signals are digitized and processed to reconstruct the image using one of many well known reconstruction techniques.

The measurement cycle used to acquire each MR signal is performed under the direction of a pulse sequence produced by a pulse sequencer. Clinically available MRI systems store a library of such pulse sequences, which can be prescribed to meet the needs of many different clinical applications. Research MRI systems include a library of clinically-proven pulse sequences, and also enable the development of new pulse sequences. The MR signals acquired with an MRI system are signal samples of the subject of the examination in Fourier space, or what is often referred to in the art as "k-space." Each MR measurement cycle, or pulse sequence, typically samples a portion of k-space along a sampling trajectory characteristic of that pulse sequence.

Because it requires time to acquire a complete k-space MR data set, subject motion presents a problem in many clinical applications. Motion due to respiration, cardiac motion, or peristalsis can produce image artifacts such as blurring or ghosting. For example, noninvasive evaluation of coronary artery disease ("CAD") has been a major goal of coronary MRI. Due to the small diameter of the coronary arteries, a high spatial resolution coronary MRI is required for the accurate visualization of the arteries. However, this has been difficult to accomplish because the coronary arteries are in constant motion due to the cardiac and respiratory cycles.

There are many strategies used to suppress such artifacts caused by subject motion. These include cardiac or respiratory gating techniques that acquire MR data only during certain phases of the cardiac or respiratory cycle. For example, to correct for cardiac motion during coronary MRI, segments of k-space lines are acquired during a short diastolic rest period of the right coronary artery in each cardiac cycle. Thus, the subject is scanned while in a particular position, but the overall scan time is increased substantially because MR data is not acquired over substantial portions of each motion cycle.

Another technique for dealing with subject motion is to interleave so-called "navigator" pulse sequences into the scan to measure subject motion. Navigator pulse sequences may be used during a scan to periodically acquire subject motion information with which the acquired k-space MR image data may be retrospectively corrected. The interleaved navigator pulse sequences, however, can add considerable scan time and in some cases they can disrupt the magnetization equilibrium required by imaging pulse sequences.

As an example, a coronary MRI acquisition is typically performed during free-breathing with a respiratory motion compensation algorithm. A diaphragmatic navigator is used to measure the right hemi diaphragm ("RHD") motion during the acquisition and to gate and correct for the respiratory motion of the heart. More specifically, before the acquisition of each k-space segment, the location of the RHD is monitored by the diaphragmatic navigator. If k-space segments are acquired when the RHD position is within a gating window timed around the respiratory end-expiration, the k-space segments are accepted for image reconstruction; otherwise, the k-space segments are rejected and reacquired in the next cardiac cycle. Typically, a five millimeter ("mm") end expiratory gating window is used to gate data because increasing the window greatly reduces the accuracy of the factor used for correcting respiratory-induced heart motion. While this acceptance/rejection approach successfully suppresses the respiratory motion of the heart, it is hindered by low respiratory efficiency (defined as the percentage of k-space segments acquired within the gating window) that results from using such a narrow gating window and variability in the subject's breathing pattern. Low navigator efficacies, often around 30-50%, result in prolonged scan time and incomplete scans, making the acquisition of high-resolution cardiac images impractical.

Several methods have been proposed to increase the size of the gating window and thereby increase gating efficiency. For example, k-space weighting and phase ordering techniques, as well as a diminishing variance algorithm, have been shown to improve image quality over the conventional acceptance/rejection approach discussed above by using a larger gating window. However, the effectiveness of these techniques is based on the subject's breathing pattern; thus, changes in the subject's respiratory pattern can significantly impact the gating efficiency.

Self-gating navigators have also been proposed to estimate the respiratory motion of the heart directly from the acquired k-space lines rather than the RHD motion. However, these techniques only account for respiratory motion of the heart along the superior-inferior ("SI") direction. The motion of the heart along anterior-posterior ("AP") and right-left ("RL") directions cannot be ignored for a gating window greater than seven mm and, therefore, must be accounted for in a motion compensation algorithm. Some three-dimensional navigators have been proposed to correct for the motion of the heart along the SI, AP, and RL directions. Also, rigid and affine transformations and non-rigid motion models have been used to estimate the respiratory motion of the heart before acquisition of k-space segments, and to correct the acquired k-space segments based on the estimated motion model. However, these algorithms involve either acquiring auxiliary pulses before the acquisition of k-space segments to generate a low resolution image and to estimate and correct for the heart respiratory motion, or modifying the k-space sampling scheme from Cartesian to radial to generate the low resolution image from the acquired inner k-space lines and to correct for the respiratory motion of the heart.

It would therefore be desirable to provide a method for acquiring high-resolution cardiac images and accurately compensating for respiratory motion. More specifically, it would be desirable to widen the gating window for acquiring data, thereby increasing navigator efficiency and shortening scan time, without respiratory-induced heart motion artifacts.

SUMMARY OF THE INVENTION

The present invention overcomes the aforementioned drawbacks by providing a respiratory motion compensation technique for magnetic resonance imaging ("MRI"), including cardiac MRI. The technique accurately compensates for respiratory-induced motion in MRI without prolonging scan acquisition time or compromising the image quality.

It is an aspect of the invention to provide a method for producing a motion-compensated image of a subject with an MRI system. An MRI system is used to acquired k-space data and navigator data from a subject. The k-space data is sorted into a plurality of data bins using the navigator data. A motion correction parameter is estimated for each data bin and is applied to the respective k-space data in that bin. The corrected k-space data segments are then combined to form a corrected k-space data set, from which an image is reconstructed. The process may be iteratively repeated until an image quality metric is optimized; for example, until an image sharpness measure is sufficiently maximized.

The foregoing and other aspects and advantages of the invention will appear from the following description. In the description, reference is made to the accompanying drawings which form a part hereof, and in which there is shown by way of illustration a preferred embodiment of the invention. Such embodiment does not necessarily represent the full scope of the invention, however, and reference is made therefore to the claims and herein for interpreting the scope of the invention.

DETAILED DESCRIPTION OF THE INVENTION

A method for acquiring high-resolution magnetic resonance images while accurately compensating for physiological subject motion is provided. By way of example, acquired k-space data is compensated for respiratory-induced subject motion. Navigator efficiency is increased and scan time is decreased by using a widened gating window for acquiring k-space data. Importantly, these benefits are realized without introducing respiratory-induced motion artifacts, such as respiratory-induced motion artifacts.

A retrospective motion compensation algorithm is provided for whole-heart coronary magnetic resonance imaging ("MRI"), in which the size of the gating window may be widened up to, for example, fifteen millimeters without compromising image quality. Unlike previous methods, the method of the present invention does not require extra prepulses for acquiring low resolution images to correct for the motion-corrupted k-space lines. The provided method is also compatible with any kind of data acquisition and k-space profile ordering techniques, and can reduce scan acquisition time by improving the scan efficiency up to ninety-two percent. The method of the present invention is suitable for correcting translational motion of respiratory-induced heart motion, as well as any the physiological motion of other organs in the body affected by translational motion.

Figure 1:
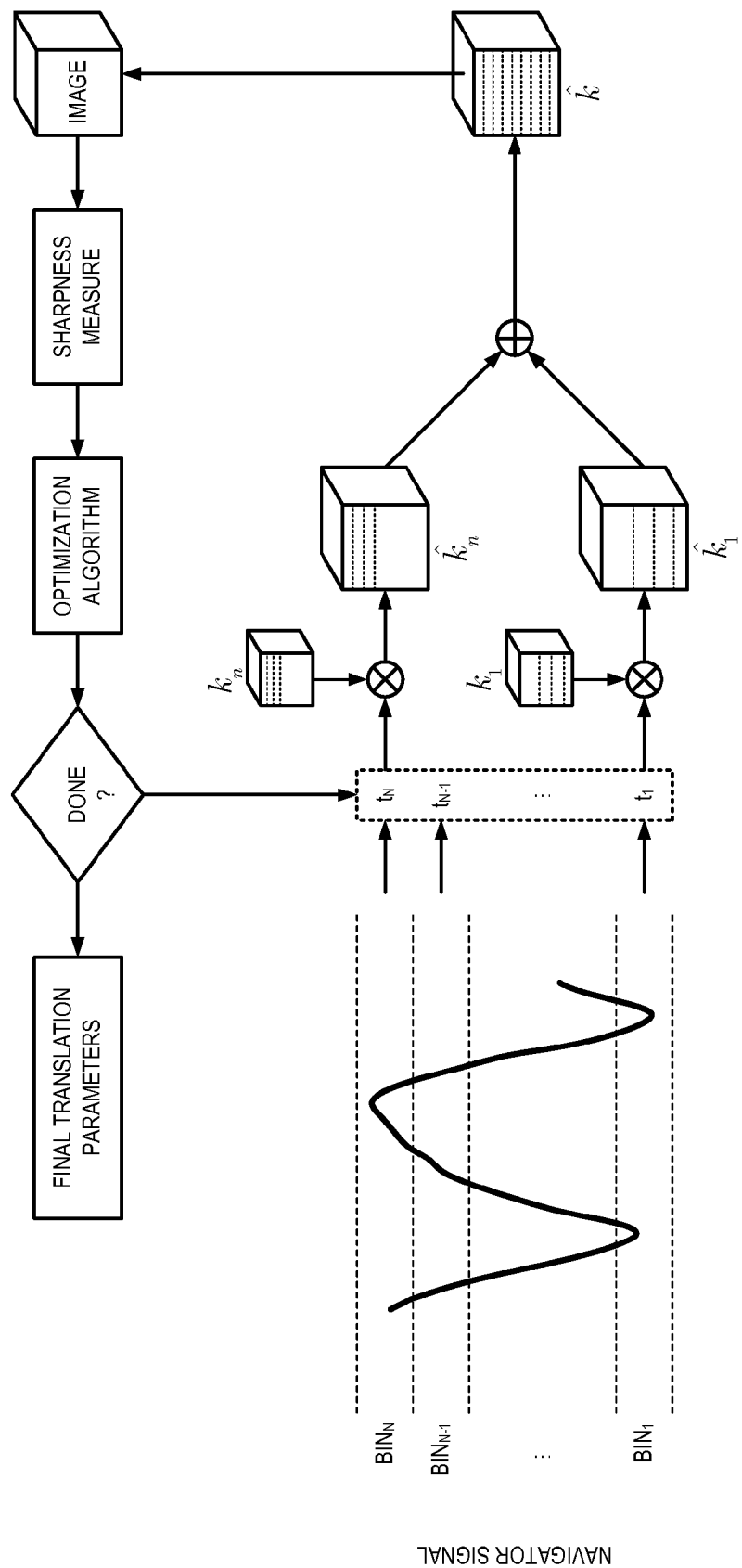
FIG. 1 is a pictorial representation of an exemplary motion compensation algorithm employed by an MRI system when practicing the present invention.

An exemplary motion compensation algorithm employed when practicing the present invention is illustrated schematically in FIG. 1. In general, data is acquired within a gating window, such as a 15 mm gating window, and is corrected with tracking factors in an iterative manner to reconstruct high-resolution images without respiratory-induced heart motion artifacts. Each tracking factor is respectively assigned to a specific respiratory cycle position. More specifically, a respiratory motion pattern measured by a diaphragmatic navigator is used to sort k-space lines acquired at different states of the respiratory cycle into separate bins. A three-dimensional translation parameter is assigned to correct the k-space segments acquired in each respective bin. The sharpness of the image reconstructed from the corrected k-space lines from all bins is measured and passed to an optimization algorithm to update the translation parameters, which can then be reapplied to again correct the k-space segments, for maximizing the sharpness of the image.

By way of example, the right hemi diaphragm ("RHD"), as measured by a diaphragmatic navigator, can be divided into N evenly spaced segments. By way of example, N may equal fifteen, and the RHD may be divided into fifteen, one millimeter segments while using a fifteen millimeter gating window. Each of the N segments can relate to a specific bin and can represent a respiratory state of the patient. For example, bin 1 and bin N can correspond to the end-expiratory and end-inspiratory states, respectively. The k-space segments, acquired immediately after the navigator, can then be assigned into a respective bin based on the RHD positions at which they are acquired. This can result in N three-dimensional k-space datasets, each of which is not completely filled.

Subsequently, a transformation model, $t_n$, including three-dimensional translation parameter, $$[t_x, t_y, t_z],$$

can be calculated for each of the N bins. An iterative gradient descent algorithm can then be used to determine the optimum transformation parameters by maximizing the sharpness of the image reconstructed from the corrected k-space segments. By way of example, a Tenengrad function or another global image sharpness measure can be used to calculate the sharpness of the image. For example, other sharpness measures such as image entropy may also be used. The Tenengrad function first calculates the image gradient using the Sobel kernel as follows:

$$\partial img(x,y,z) = img(x,y,z) * s \quad (1);$$

Where s is the Sobel kernel defined as:

$$s(:,:,-1) = \begin{bmatrix} 1 & 2 & 1 \\ 2 & 4 & 2 \\ 1 & 2 & 1 \end{bmatrix} \qquad (2)$$

$$s(:,:,0) = \begin{bmatrix} 0 & 0 & 0 \\ 0 & 0 & 0 \\ 0 & 0 & 0 \end{bmatrix}$$

$$s(:,:,1) = \begin{bmatrix} -1 & -2 & -1 \\ -2 & -4 & -2 \\ -1 & -2 & -1 \end{bmatrix};$$

The variance of the gradient image, $\partial img(x,y,z)$, may then computed as the sharpness measure.

Since, in the preceding example, there are fifteen bins and each bin has a three-dimensional translation parameter, there are a maximum of forty-five parameters for estimation in the iterative gradient descent algorithm. Due to the high complexity of simultaneous estimation of all parameters, a sequential iterative gradient descent algorithm can be used to sequentially estimate the translation parameter of each bin.

Figure 2:
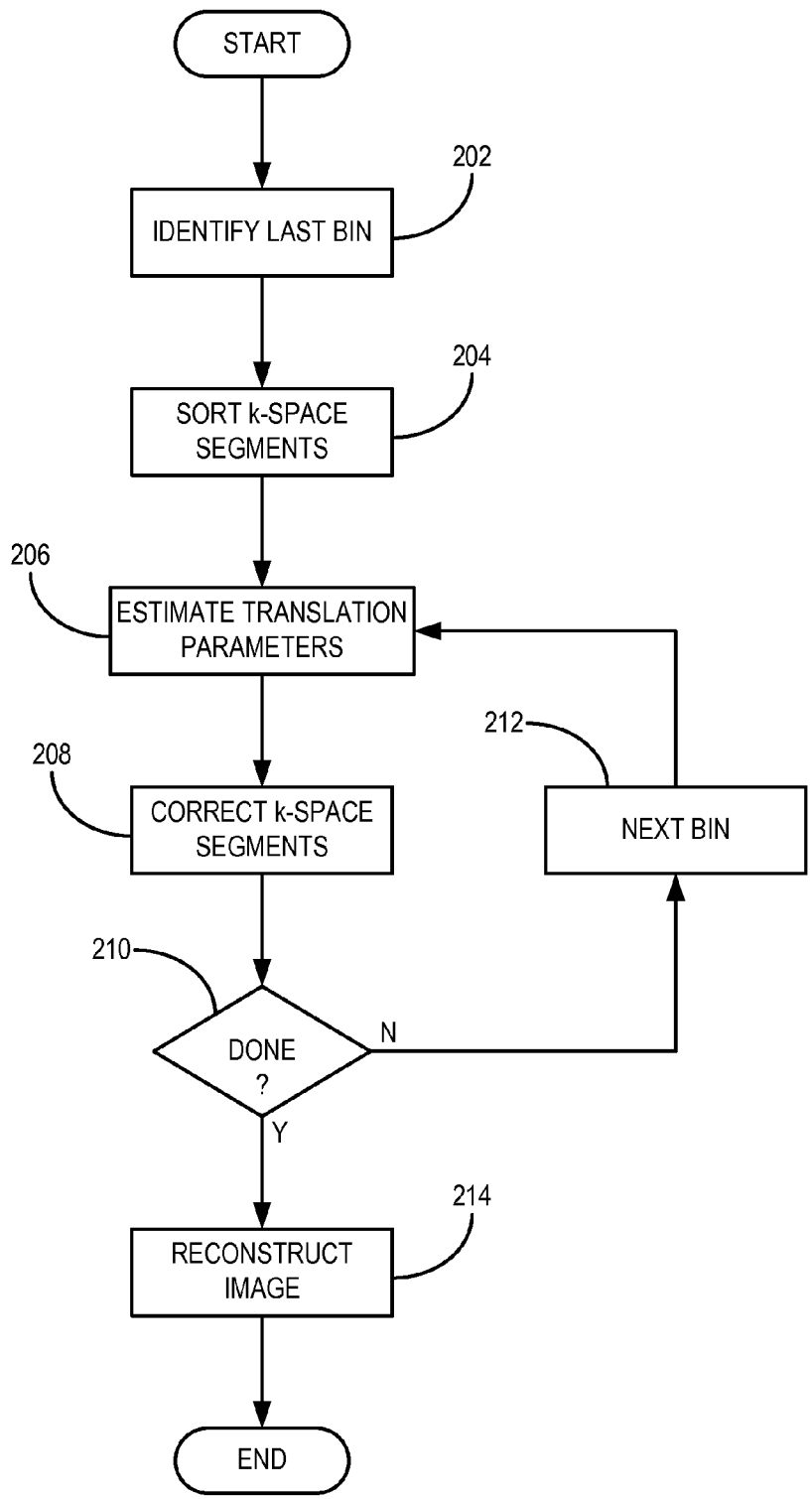
FIG. 2 is a flowchart setting forth the steps of an example of a method for motion compensation in accordance with an embodiment of the invention.

Referring now to FIG. 2, a flowchart setting forth an example of a method for respiratory-induced motion compensation of high-resolution magnetic resonance images is illustrated. As shown in FIG. 2, in the first step of the process, step 202, the last bin corresponding to the respiratory end-expiration is determined. Next, at step 204, k-space segments acquired at the last bin are sorted out for correction. Following the sorting, at step 206, translation parameters corresponding to the last bin are estimated by the iterative gradient descent optimization algorithm, so that the image reconstructed from the k-space lines of all bins is maximized. At step 208, the k-space segments acquired at the last bin by the estimated translation parameters are then corrected. A determination is then made at decision block 210 as to whether all of the desired bins have been processed. If not, the next bin is selected, as indicated at step 212. For example, the subsequent bin is considered the last bin corresponding to the end-expiration. The process reverts back to step 206 until all bins are processed.

Since a sequential iterative gradient descent algorithm is used for sequentially estimating the translational parameter of each bin, this procedure can be repeated, such as for three times, until all the translation parameters converge to a solution.

After all of the desired bins have been processed, an image is reconstructed, as indicated at step 214. In the final stage of the reconstruction, the calculated translation parameters can be used to correct the phase of k-space segments acquired at each bin as follows:

$$\hat{k}_i(k_x, k_y, k_z) = k_i \cdot \exp\left(\frac{2\pi k_x}{FOV_x}t_x + \frac{2\pi k_y}{FOV_y}t_y + \frac{2\pi k_z}{FOV_z}t_z\right); \qquad (3)$$

where $k_i$ is the k-space segment acquired at the $i^{th}$ and $FOV_x$, $FOV_y$, and $FOV_z$ are the fields of view along the x-direction, y-direction, and z-direction, respectively. By way of example, the x-direction may correspond to the readout direction, the y-direction may correspond to the phase-encoding direction, and the z-direction may correspond to the slice-encoding direction. After correction of the k-space segments at each bin, the full k-space can be reconstructed as:

$$\hat{k}(k_x, k_y, k_z) = \sum_{i=1}^{N} \hat{k}_i(k_x, k_y, k_z); \qquad (4)$$

where N is the number of bins.

Given the correct transformation, the image reconstructed by the corrected k-space segments should bear maximum sharpness without any ghosting and blurring artifacts caused by respiratory motion. Because the correct transformation models are not known at the beginning, the sharpness of the image can only be optimized through the iterative process. In addition, increasing the gating window, for example to fifteen mm, in comparison to the conventional five mm gating window can result in increased navigator efficiency (e.g., approximately 91 percent to approximately 100 percent, as further described below) and shortened scan time, enabling the acquisition of high-resolution cardiac images.

Thus, a new motion compensation technique for the correction of respiratory-induced heart motion in whole-heart coronary magnetic resonance imaging is provided. The method is also applicable to other sources of physiological motion. The provided method uses navigator information to sort k-space lines into N different bins with a set size, such as 1 mm, in the respiratory cycle. A three-dimensional translation parameter is calculated for each bin to correct the k-space lines acquired at that bin. The three-dimensional translation parameters are iteratively estimated using a sequential gradient descent algorithm such that the image reconstructed by the corrected k-space lines from all bins has maximum sharpness.

In the current implementation, a three-dimensional translation model is assigned to each bin since the translation of the heart has been shown to be the major components of the respiratory-induced heart motion. The provided method, however, may also be extended to model the respiratory motion of the heart with affine transformations.

In whole-heart acquisitions, an acquisition window of 80-100 ms in each cardiac cycle is used to acquire multiple k-space lines. This acquisition window can potentially be widened for the further reduction of image acquisition time. In such an instance, both ECG and diaphragmatic navigator information may be used to sort the acquired k-space lines into a two-dimensional grid. To each grid, an affine transformation may be assigned to model and correct both the cardiac and respiratory motion.

The provided method can also be combined with parallel imaging techniques, such as SENSE and GRAPPA, and also with other imaging techniques, such as compressed sensing, for further reduction of scan time. A reliable reduction factor of two from SENSE, GRAPPA, and compressed sensing can reduce scan acquisition time of whole-heart coronary MRI.

In the current implementation, a diaphragmatic navigator is used to detect the respiratory motion; however, self-gating navigators or information acquired from multiple coils can also be used to detect the presence of motion and to bin the k-space lines. The provided method can be performed separately on different coils to estimate individual translation parameters for each coil, or the method can be performed the average image generated from all the coils and the estimated translation parameters are applied to the k-space signals measured by all the coils.

Figure 3:
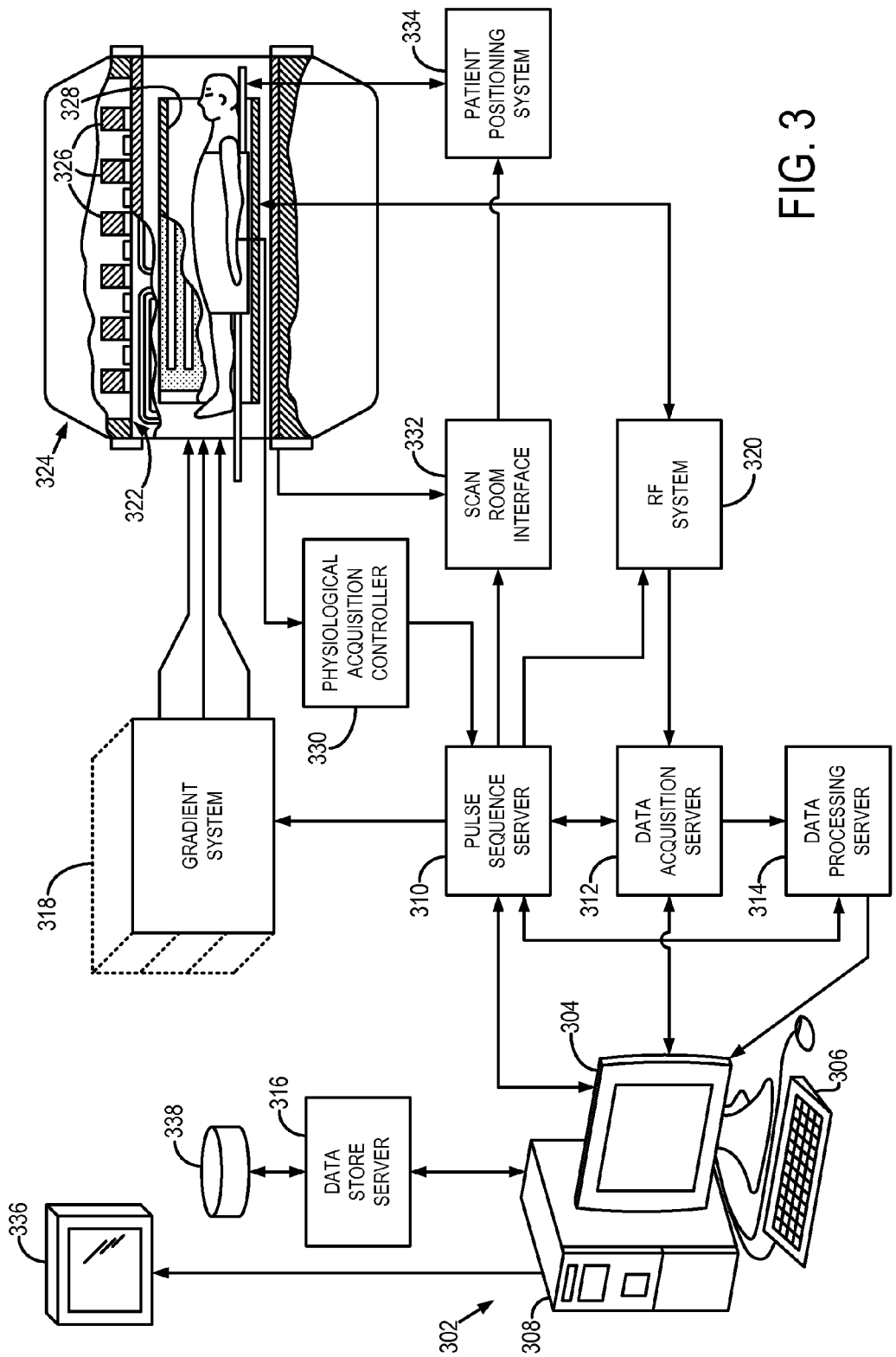
FIG. 3 is a block diagram of an example of an MRI system that may employ the present invention.

Referring particularly now to FIG. 3, an exemplary magnetic resonance imaging ("MRI") system 300 is illustrated. The MRI system 300 includes a workstation 302 having a display 304 and a keyboard 306. The workstation 302 includes a processor 308, such as a commercially available programmable machine running a commercially available operating system. The workstation 302 provides the operator interface that enables scan prescriptions to be entered into the MRI system 300. The workstation 302 is coupled to four servers: a pulse sequence server 310; a data acquisition server 312; a data processing server 314; and a data store server 316. The workstation 302 and each server 310, 312, 314, and 316 are connected to communicate with each other.

The pulse sequence server 310 functions in response to instructions downloaded from the workstation 302 to operate a gradient system 318 and a radiofrequency ("RF") system 320. Gradient waveforms necessary to perform the prescribed scan are produced and applied to the gradient system 318, which excites gradient coils in an assembly 322 to produce the magnetic field gradients $G_x$, $G_y$, and $G_z$ used for position encoding MR signals. The gradient coil assembly 322 forms part of a magnet assembly 324 that includes a polarizing magnet 326 and a whole-body RF coil 328.

RF excitation waveforms are applied to the RF coil 328, or a separate local coil (not shown in FIG. 3), by the RF system 320 to perform the prescribed magnetic resonance pulse sequence. Responsive MR signals detected by the RF coil 328, or a separate local coil (not shown in FIG. 3), are received by the RF system 320, amplified, demodulated, filtered, and digitized under direction of commands produced by the pulse sequence server 310. The RF system 320 includes an RF transmitter for producing a wide variety of RF pulses used in MR pulse sequences. The RF transmitter is responsive to the scan prescription and direction from the pulse sequence server 310 to produce RF pulses of the desired frequency, phase, and pulse amplitude waveform. The generated RF pulses may be applied to the whole body RF coil 328 or to one or more local coils or coil arrays (not shown in FIG. 3).

The RF system 320 also includes one or more RF receiver channels. Each RF receiver channel includes an RF amplifier that amplifies the MR signal received by the coil 328 to which it is connected, and a detector that detects and digitizes the I and Q quadrature components of the received MR signal. The magnitude of the received MR signal may thus be determined at any sampled point by the square root of the sum of the squares of the I and Q components:

$$M = \sqrt{I^2 + Q^2} \tag{5}$$

and the phase of the received MR signal may also be determined:

$$\varphi = \tan^{-1}\left(\frac{Q}{I}\right). \tag{6}$$

The pulse sequence server 310 also optionally receives patient data from a physiological acquisition controller 330. The controller 330 receives signals from a number of different sensors connected to the patient, such as electrocardiograph ("ECG") signals from electrodes, or respiratory signals from a bellows or other respiratory monitoring device. Such signals are typically used by the pulse sequence server 310 to synchronize, or "gate," the performance of the scan with the subject's heart beat or respiration.

The pulse sequence server 310 also connects to a scan room interface circuit 332 that receives signals from various sensors associated with the condition of the patient and the magnet system. It is also through the scan room interface circuit 332 that a patient positioning system 334 receives commands to move the patient to desired positions during the scan.

The digitized MR signal samples produced by the RF system 320 are received by the data acquisition server 312. The data acquisition server 312 operates in response to instructions downloaded from the workstation 302 to receive the real-time MR data and provide buffer storage, such that no data is lost by data overrun. In some scans, the data acquisition server 312 does little more than pass the acquired MR data to the data processor server 314. However, in scans that require information derived from acquired MR data to control the further performance of the scan, the data acquisition server 312 is programmed to produce such information and convey it to the pulse sequence server 310. For example, during prescans, MR data is acquired and used to calibrate the pulse sequence performed by the pulse sequence server 310. Also, navigator signals may be acquired during a scan and used to adjust the operating parameters of the RF system 320 or the gradient system 318, or to control the view order in which k-space is sampled. The data acquisition server 312 may also be employed to process MR signals used to detect the arrival of contrast agent in a magnetic resonance angiography ("MRA") scan. In all these examples, the data acquisition server 312 acquires MR data and processes it in real-time to produce information that is used to control the scan.

The data processing server 314 receives MR data from the data acquisition server 312 and processes it in accordance with instructions downloaded from the workstation 302. Such processing may include, for example: Fourier transformation of raw k-space MR data to produce two or three-dimensional images; the application of filters to a reconstructed image; the performance of a backprojection image reconstruction of acquired MR data; the generation of functional MR images; and the calculation of motion or flow images.

Images reconstructed by the data processing server 314 are conveyed back to the workstation 302 where they are stored. Real-time images are stored in a data base memory cache (not shown in FIG. 3), from which they may be output to operator display 312 or a display 336 that is located near the magnet assembly 324 for use by attending physicians. Batch mode images or selected real time images are stored in a host database on disc storage 338. When such images have been reconstructed and transferred to storage, the data processing server 314 notifies the data store server 316 on the workstation 302. The workstation 302 may be used by an operator to archive the images, produce films, or send the images via a network to other facilities.

The present invention has been described in terms of one or more preferred embodiments, and it should be appreciated that many equivalents, alternatives, variations, and modifications, aside from those expressly stated, are possible and within the scope of the invention.

The invention claimed is:

1. A method for producing an image of a subject with a magnetic resonance imaging (MRI) system, the steps of the method comprising:
   a) acquiring, with the MRI system, k-space data from a subject;
   b) acquiring, with the MRI system, navigator data from a subject;
   c) sorting the acquired k-space data into a plurality of different data bins using the acquired navigator data;

d) estimating translational motion correction parameters for each of the plurality of different data bins, each translational motion correction parameter indicating translational motion of the subject that occurred during step a);
e) correcting the sorted k-space data in each of the plurality of different data bins by applying the translational motion correction parameters estimated for a respective data bin to the k-space data in that data bin;
f) combining the corrected k-space data; and
g) reconstructing an image from the corrected k-space data combined in step f).

2. The method as recited in claim 1 further comprising measuring an image quality parameter of the image reconstructed in step g).

3. The method as recited in claim 2 in which the image quality parameter is a measure of an image sharpness of the reconstructed image.

4. The method as recited in claim 2 in which steps d)-g) are repeated iteratively while optimizing the measured image quality parameter.

5. The method as recited in claim 1 in which step c) includes dividing the acquired navigator data into a number of different segments.

6. The method as recited in claim 5 in which the number of different segments is selected in relation to a gating window.

7. The method as recited in claim 6 in which the gating window is a fifteen millimeter gating window and the number of different segments is fifteen.

8. The method as recited in claim 1 in which step c) includes sorting the acquired k-space data into a plurality of different data bins that are each associated with a different respiratory state.

9. A magnetic resonance imaging (MRI) system comprising:
   a magnet system configured to generate a polarizing magnetic field about at least a portion of a subject arranged in the MRI system;
   a plurality of gradient coils configured to apply at least one gradient field to the polarizing magnetic field;
   a radio frequency (RF) system configured to apply an RF field to the subject and to acquire magnetic resonance (MR) image data therefrom;
   a computer system programmed to:
     direct the RF system to acquire MR image data from a subject;
     direct the RF system to acquire navigator data from the subject;
     sort the acquired MR image data into a plurality of different data bins using the acquired navigator data;
     estimate translational motion correction parameters for each of the plurality of different data bins, each translational motion correction parameter indicating translational motion of the subject that occurred when the MR image data were acquired;
     correct the sorted MR image data using the translational motion correction parameters estimated for respective ones of the plurality of different data bins;
     combine the corrected MR image data; and
     reconstruct an image from the combined MR image data.

10. The MRI system as recited in claim 9 in which the computer system is further programmed to measure an image quality parameter of the reconstructed image, and to iteratively update the motion correction parameters while optimizing the measured image quality parameter.

11. The MRI system as recited in claim 10 in which the image quality parameter is a measure of an image sharpness of the reconstructed image.

12. The MRI system as recited in claim 9 in which the computer system is programmed to sort the acquired MR image data by dividing the acquired navigator data into a number of different segments.

13. The MRI system as recited in claim 12 in which the number of different segments is selected in relation to a gating window.

14. The MRI system as recited in claim 13 in which the gating window is a fifteen millimeter gating window and the number of different segments is fifteen.

15. The MRI system as recited in claim 9 in which the computer system is programmed to sort the acquired MR image data into a plurality of different data bins that are each associated with a different respiratory state.

* * * * *